(12) United States Patent
Chou

(10) Patent No.: US 8,138,170 B2
(45) Date of Patent: Mar. 20, 2012

(54) IMMUNOSUPPRESSIVE NINGALIN COMPOUNDS

(75) Inventor: Ting-Chao Chou, New York, NY (US)

(73) Assignee: Memorial Sloan-Kettering Cancer Center, New York, NY (US)

(*) Notice: Subject to any disclaimer, the term of this patent is extended or adjusted under 35 U.S.C. 154(b) by 1136 days.

(21) Appl. No.: 11/661,522

(22) PCT Filed: Aug. 29, 2005

(86) PCT No.: PCT/US2005/030532
§ 371 (c)(1), (2), (4) Date: Sep. 19, 2007

(87) PCT Pub. No.: WO2006/026496
PCT Pub. Date: Mar. 9, 2006

(65) Prior Publication Data
US 2008/0194543 A1    Aug. 14, 2008

Related U.S. Application Data

(60) Provisional application No. 60/605,326, filed on Aug. 27, 2004.

(51) Int. Cl.
  *A61K 31/55* (2006.01)
  *A61K 31/403* (2006.01)
  *A61K 31/40* (2006.01)
  *A61P 37/00* (2006.01)
  *A01N 43/00* (2006.01)
  *A01N 43/38* (2006.01)
  *A01N 43/46* (2006.01)

(52) U.S. Cl. .................. 514/214.01; 514/411; 514/429

(58) Field of Classification Search ............. 514/214.01, 514/411, 429
See application file for complete search history.

(56) References Cited

U.S. PATENT DOCUMENTS 5,852,033 A * 12/1998 Puentes et al. ............... 514/283

OTHER PUBLICATIONS

Rathod, (http://www.suite101.com/content/why-organ-transplants-fail-a122888), 2009.*
Opelz et al. (Am J of Transplantation, 2003, 4, 222-230), 2003.*
Moore (http://www.suite101.com/ content /immunosuppressant-drugs-a25374), 2007.*
Nancy Ross-Flanigan, (http://www.surgeryencyclopedia.com/Fi-La/Immunosuppressant-Drugs.html), 2011.*
Fishman (NEJM, 338, 24, p. 1741-1751), 1988.*
Boger, Dale, L. et al: "Total Syntheses of Ningalin A, Lamellarin O, Lukianol A, and Permethyl Stomiamide A Utilizing Heterocyclic Azadiene Diels—Alder Reactions" J. Am. Chem. Soc. 1999, 121, 54-62.
Boger, Dale, L. et al: "Total Synthesis of Ningalin B Utilizing a Heterocyclic Azadiene Diels—Alder Reaction and Discovery of a New Class of Potent Multidrug Resistant (MDR) Reversal Agents" J. Org. Chem. 2000, 65, 2479-2483.
Bruening, R. C.; et al: Isolation and Structure of Tunichrome B-1, a Reducing Blood Pigment from the Tunicate *Ascidia nigra* L. . J. Am. Chem. Soc. 1985, 107, 5298-5300.
Bruening, R. C.; et al: "Isolation of Tunichrome B-1, A Reducing Blood Pigment of the Sea Squirt, *Ascidia nigra*" J. Nat. Prod. 1986, 49, 193-204.
Bayer, E; et al: "Structure of the Tunichrome of Tunicates and its Role in Concentrating Vanadium" Angew. Chem. Int. Ed. Engl. 1992, 31, 52-54.
Oltz, E. M.; et al: "The Tunichromes. A Class of Reducing Blood Pigments from Sea Squirts: Isolation, Structures, and Vanadium Chemistry" J. Am. Chem. Soc. 1988, 110, 6162-6172.
Ryan, D. E.; et al: "Reactivity of Tunichromes: Reduction of Vanadium(V) and Vanadium(IV) to Vanadium(III) at Neutral pH" J. Am. Chem. Soc. 1992, 114, 9659-9660.
Taylor, Steven, W. et al: "Novel 3,4-Di- and 3,4,5-Trihydroxyphenylalanine-Containing Polypeptides from the Blood Cells of the Ascidians Ascidia ceratodes and Molgula manhattensis" Archives of Biochemistry and Biophysics vol. 324, No. 2, Dec. 20, pp. 228-240, 1995.
Notification Concerning Transmittal of International Preliminary Report on Patentability (Chapter 1 of the Patent Cooperation Treaty), 2007.
International Preliminary Report of Patentability, 2006.
Written Opinion of the International Searching Authority, 2007.

* cited by examiner

*Primary Examiner* — Sreeni Padmanabhan
*Assistant Examiner* — Uma Ramachandran
(74) *Attorney, Agent, or Firm* — Edwards Wildman Palmer LLP; Peter C. Lauro, Esq.; Melissa Hunter-Ensor, Esq.

(57) ABSTRACT

The present invention provides compositions and methods comprising ningalins for use in modulating immune responses to infection, injury, allergy and/or transplantation.

12 Claims, 3 Drawing Sheets

IMMUNOSUPPRESSIVE NINGALIN COMPOUNDS

RELATED APPLICATIONS/PATENTS & INCORPORATION BY REFERENCE

This application is filed under 35 U.S.C. §371 as the U.S. national phase application of International Application No. PCT/US2005/030532, having an international filing date of Aug. 29, 2005 and claiming priority from U.S. application Ser. No. 60/605,326, filed on Aug. 27, 2004, the contents of which are hereby expressly incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF POTENTIAL GOVERNMENT INTEREST

The United States Government has certain rights in this invention by virtue of grant number CA-08748 from the National Institutes of Health.

FIELD OF THE INVENTION

The present invention relates to ningalin compounds and methods for use in modulating immune responses. Compositions and methods of the invention can be used, for example, to provide immunosuppression during transplantation.

BACKGROUND OF THE INVENTION

Inflammatory reactions can provide an essential defense to infection and injury. At the same time, many human diseases or treatments are aggravated by excessive inflammatory reactions brought on by immune responses (e.g., immune responses to organ transplantation). Presently, development of specific and efficacious anti-inflammatory treatment modalities is challenging. For example, use of pharmacologic anti-inflammatory agents (e.g., corticosteroids, NSAIDs, and cytokine antagonists) or immunosuppressive agents (e.g., cyclosporin A, FK 506 and rapamycin) is frequently complicated by adverse events limiting their clinical utility. Therefore, identification of biocompatible agents that reduce immune responses, and preferably inflammation, has important therapeutic implications.

Ningalins comprise a family of 3,4-dihydroxyphenylalanine (DOPA)-derived o-catechol metabolites that include the tunichromes (Bruening, R. C.; et al. J. Am. Chem. Soc. 1985, 107, 5289; Bruening, R. C.; et al. J. Nat. Prod. 1986, 49, 193; Bayer, E; et al. Angew. Chem. Int. Ed. Engl. 1992, 31, 52; Oltz, E. M.; et al. J. Am. Chem. Soc. 1988, 110, 6162; Ryan, D. E.; et al. J. Am. Chem. Soc. 1992, 114, 9659; Taylor, S. W.; et al. Arch. Biochem. Biophys. 1995, 324, 228). Ningalins are believed to be potent reversing agents of multidrug resistance. Ningalins were not heretofore known to be viable therapeutic candidates for reducing inflammation or mediating immunosuppression.

SUMMARY OF THE INVENTION

It has now been shown that compositions comprising ningalins can be provided to a subject in need thereof to modulate immune responses to, for example, infection, injury, allergy and/or transplantation.

In one aspect, the present invention provides compositions comprising pharmaceutical formulations of one or more ningalins, in an amount sufficient to decrease an adverse immune response.

Ningalins of the invention can include, but are not limited to N1, N2, N3, N4, N5, and N6 as depicted in FIG. 1, Ningalin A, Ningalin B and analogs thereof.

The adverse immune response can comprise inflammatory cell activation, proliferation, and/or accumulation.

Inflammatory cells of the invention can include, but are not limited to, leukocytes, lymphocytes, natural killer cells, and antigen-presenting cells. Leukocytes can include neutrophils, basophils, mast cells, eosinophils, monocytes, and macrophages. Lymphocytes can include B-lymphocytes and T-lymphocytes. The antigen-presenting cells can include dendritic cells and stromal cells.

In specific embodiments, the pharmaceutical formulations comprise from about 50 to about 4000 mg/m$^2$ of one or more ningalins.

In one embodiment, ningalins of the invention are administered to a subject (e.g., a human subject) having, or at risk of having, an adverse immune response.

In another embodiment, the adverse immune response can be attributed to various diseases and conditions affecting one or more target sites. Ningalins of the invention can be provided directly to the target site in a subject. Target sites of the invention can comprise one or more organs or organ systems including, but not limited to, the peripheral nervous system, the central nervous system, skin, appendix, gastro intestinal tract (including but not limited to esophagus, duodenum, and colon), respiratory/pulmonary system (including but not limited to lung, nose, pharynx, larynx), eye, genitalia/reproductive system, gums, heart, liver/biliary ductal system, renal system (including but not limited to kidneys, urinary tract, bladder), connective tissue (including but not limited to joints, cartilage), cardiovascular system, breast, lymphatic system, muscle, ear, endocrine/exocrine system (including but not limited to lacrimal glands, salivary glands, thyroid gland, pancreas), bone/skeletal system, hematological cells and bone marrow.

Target sites of the invention can also comprise transplanted and implanted organs, tissues, blood or synthetic materials that bring about an immune response. In a specific embodiment, organs, tissues, blood or synthetic materials can be pre-treated with ningalins of the invention to prevent an adverse immune response upon transplantation or implantation into a subject.

In another aspect, the present invention provides a method for modulating an adverse immune response in a subject comprising administering to the subject one or more ningalins in an amount effective to decrease the adverse immune response.

In specific embodiments, the amount effective to decrease an adverse immune response in a human subject is from about 50 to about 500 $mg/m^2$, from about 500 to about 1000 $mg/m^2$, from about 1000 to about 2000 $^{mg}/m^2$, and from about 2000 to about 4000 $^{mg}/m^2$ of one or more ningalins per dose.

The adverse immune response can result, for example, from exposure to an allergen or pathogen or transplantation of heterologous blood, organ or tissue.

Accordingly, in a specific embodiment, the present invention provides a method for inhibiting organ rejection in a subject in whom an organ has been transplanted, comprising administering to the subject an effective amount of one or more ningalins prior to, simultaneously with or following organ transplantation, in an amount effective to inhibit organ rejection.

In yet another specific embodiment, the present invention provides a method for providing immunosuppression to a subject in whom an organ has been, or will be transplanted, comprising administering to the subject one or more ningalins in an amount effective to decrease inflammatory cell activation.

In some embodiments, the adverse immune response comprises an autoimmune response.

In some embodiments, the adverse immune response includes inflammation.

Inflammation can result from inflammatory cell activation, proliferation and/or accumulation, for example, at a target site. Accordingly, in yet another aspect, the present invention provides a method of treating inflammation in a subject in need thereof comprising administering to the subject a pharmaceutical composition comprising one or more ningalins in an amount sufficient to reduce inflammatory cell accumulation.

In one embodiment, the present invention provides a method of decreasing inflammation in a subject, comprising contacting inflammatory cells undergoing or likely to undergo activation or proliferation with one or more ningalins in an amount effective to inhibit activation or proliferation of the cells.

In another embodiment, the present invention provides a method of decreasing accumulation of inflammatory cells at a target site, comprising contacting inflammatory cells undergoing or likely to undergo activation or proliferation with one or more ningalins in an amount effective to inhibit activation or proliferation of the cells.

In yet another aspect, the present invention provides a method of screening ningalin analogs for immunosuppressive activity comprising the steps of:
  a) contacting test inflammatory cells with an amount of a ningalin analog sufficient to exert a physiologic effect comprising decreasing inflammatory cell proliferation and measuring the physiologic effect on the test inflammatory cells;
  b) contacting control inflammatory cells with a ningalin and measuring the physiologic effect on the inflammatory control cells; and
  c) comparing the physiologic effect of the ningalin analog to the physiologic effect of the ningalin, wherein determination of a physiologic effect of the ningalin analog is expressed relative to that of the ningalin.

In certain embodiments, the methods of the invention further comprise obtaining the ningalin/ningalin analog used in the methods. In other embodiments, the methods of the invention further comprise synthesizing the ninalin/ningalin analog used in the methods.

In another aspect the invention provides a kit comprising a ningalin and instructions for immunosuppressive therapeutic use. In a preferred embodiment, the ningalin is present in the kit as a pharmaceutical composition comprising a therapeutically effective amount of the ningalin and a pharmaceutically acceptable carrier.

In yet another embodiment, the invention provides a composition comprising a container including a ningalin and a label or package insert with instructions for immunosuppressive therapeutic use. In a preferred embodiment, the ningalin is present in the composition as a pharmaceutical composition comprising a therapeutically effective amount of the ningalin and a pharmaceutically acceptable carrier.

In this disclosure, "comprises," "comprising," "containing" and "having" and the like can have the meaning ascribed to them in U.S. Patent law and can mean, "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

These and other objects of the invention will be described in further detail in connection with the detailed description of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings, in which.

DETAILED DESCRIPTION OF THE INVENTION

I. Definitions

A "ningalin" is a compound which possess a common 3,4-diaryl substituted pyrrole nucleus bearing a 2-carboxyl. Ningalins of the invention include but are not limited to Ningalins denoted as N1-N6 in FIG. 1, Ningalin A, Ningalin B, and analogs thereof. The phrase "a ningalin" is intended to include one or more ningalins. As used herein, the term "native ningalin" refers to Ningalin A or Ningalin B.

In certain embodiments of the invention, the ningalins of the invention are compounds of formula I

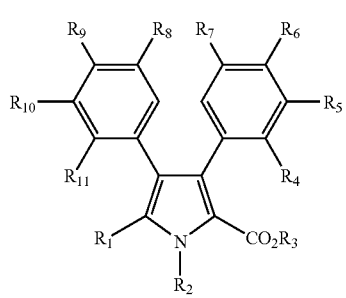

wherein:
$R_1$ is H, $CO_2R$ or $C(=O)N(R)_2$;
$R_2$ is H or $-(CH_2)_n$-Aryl; or
$R_1$ and $R_2$ taken together form a bicyclic ring;

$R_3$ is H or $C_1$-$C_{20}$ alkyl;
$R_4$ is H, OR or $O(CH_2)_nOR$; or
$R_3$ and $R_4$ taken together form a heterocycle;
$R_5$-$R_{20}$ are the same or different and each is H, $C_1$-$C_{20}$ alkyl, amino, cyano, halogen, nitro or OR;
$R_{11}$ is H, OR or $O(CH_2)_nOR$;
R is H or $C_1$-$C_{20}$ alkyl; and
n is 1, 2 or 3.

In one embodiment, the ningalins of the invention are compounds of formula IA

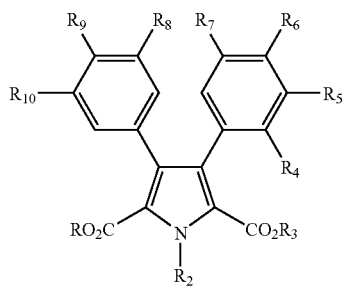

IA wherein R is H or $C_1$-$C_{20}$ alkyl;
$R_2$ is H or —$(CH_2)_n$-Aryl;
$R_3$ is H or $C_1$-$C_{20}$ alkyl;
$R_4$ is H, $C_1$-$C_{20}$ alkyl or $O(CH_2)_nOR$;
$R_5$-$R_{20}$ are the same or different and each is H, $C_1$-$C_{20}$ alkyl, amino, cyano, halogen, nitro or OR; and
n is 1, 2 or 3.

In a preferred embodiment of formula IA, R and $R_3$ are methyl, $R_2$, $R_5$ and $R_{20}$ are H, $R_4$ is $OCH_2OCH_3$, and $R_6$-$R_9$ are methoxy. In another preferred embodiment of formula IA, R and $R_3$ are methyl, $R_4$ is $OCH_2OCH_3$, $R_5$ and $R_{20}$ are H, $R_6$-$R_9$ are methoxy and $R_2$ is

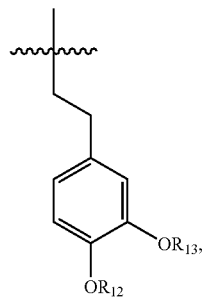

wherein $R_{12}$ and $R_{13}$ are the same or different and each is H or $C_1$-$C_{20}$ alkyl, preferably methyl.

In yet another preferred embodiment of formula IA, R and $R_3$ are methyl, $R_4$ is H, $R_5$-$R_{20}$ are methoxy and $R_2$ is

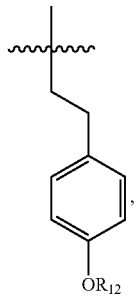

wherein $R_{12}$ is H or $C_1$-$C_{20}$ alkyl, preferably methyl.

In another embodiment, the ningalins of the invention are compounds of formula IB

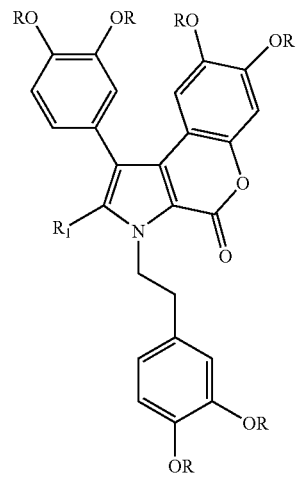

IB wherein
R is H or $C_1$-$C_{20}$ alkyl; and
$R_1$ is H, $CO_2R$ or $C(=O)N(R)_2$.

In a preferred embodiment of formula IB, R is methyl and $R_1$ is H. In another preferred embodiment of formula IB, R is methyl and $R_1$ is $CO_2H$. In yet another preferred embodiment of formula IB, R is methyl and $R_1$ is $CO_2CH_3$. In still another preferred embodiment of formula IB, R is methyl and $R_1$ is $C(=O)N(CH_3)_2$.

In another embodiment, the ningalins of the invention are compounds of formula IC

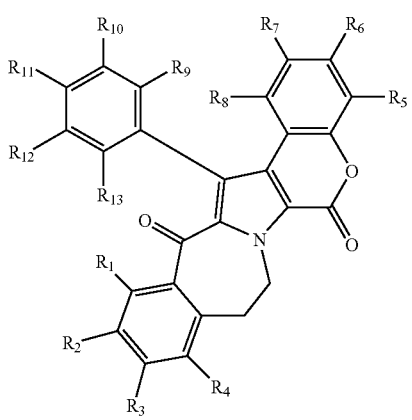

IC wherein $R_1$-$R_{13}$ are the same or different and each is H, $C_1$-$C_{20}$ alkyl, amino, cyano, halogen, nitro or OR; and R is H or $C_1$-$C_{20}$ alkyl. In a preferred embodiment of formula IC, $R_1$, $R_4$, $R_5$, $R_8$, $R_9$ and $R_{12}$ are H, and $R_2$, $R_3$, $R_6$, $R_7$, $R_{10}$ and $R_{11}$ are OR wherein R is methyl.

Figure 1:
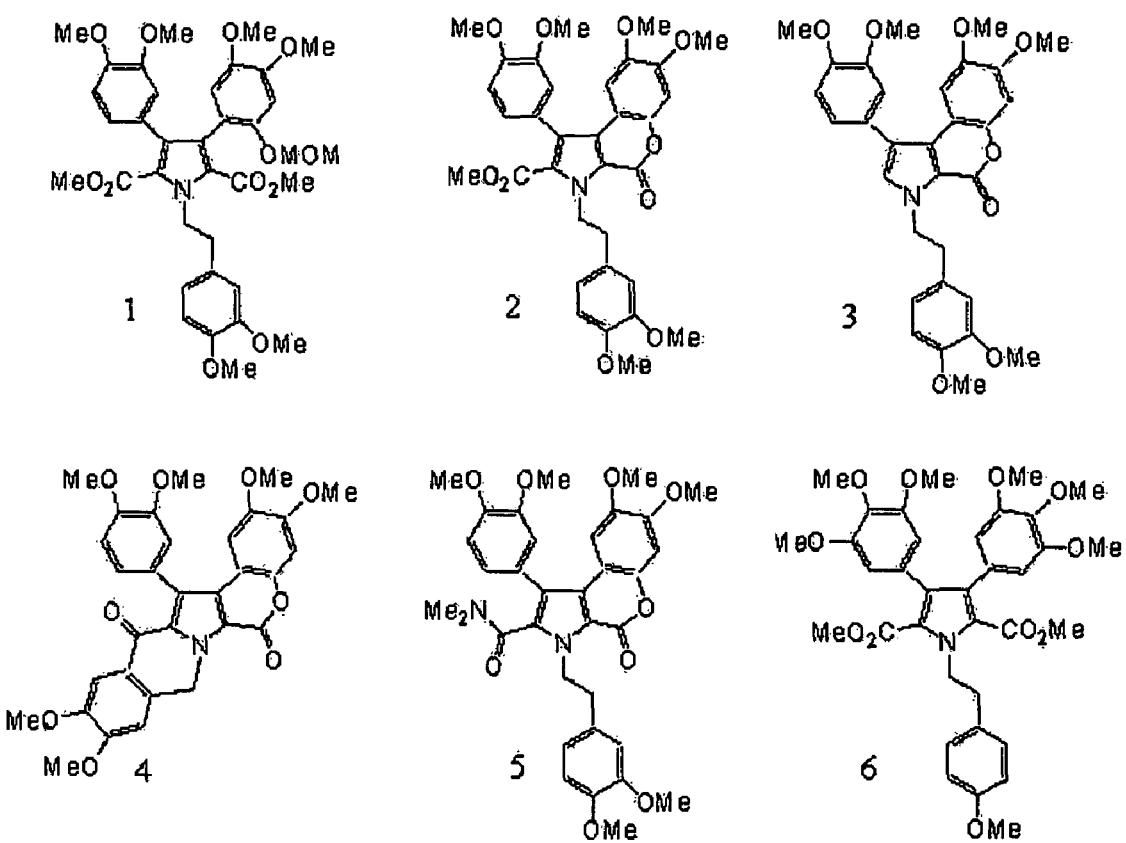
FIG. 1 depicts the structures of ningalin compounds N1, N2, N3, N4, N5, and N6.

Particularly preferred ningalins in accordance with the invention are those shown in FIG. 1 as follows: 1-[2-(4-Methoxy-phenyl)-ethyl]-3-(3,4,5-trimethoxy-2-methoxymethoxy-phenyl)-4-(3,4,5-trimethoxy-phenyl)-1H-pyrrole-2,5-dicarboxylic acid dimethyl ester (N1); 1-(3,4-Dimethoxy-phenyl)-3-[2-(3,4-dimethoxy-phenyl)-ethyl]-7,8-dimethoxy-4-oxo-3,4-dihydro-5-oxa-3-aza-cyclopenta[α]naphthalene-2-carboxylic acid methyl ester (N2); 1-(3,4-Dimethoxy-phenyl)-3-[2-(3,4-dimethoxy-phenyl)-ethyl]-7,8-dimethoxy-3H-5-oxa-3-aza-cyclopenta[α]naphthalen-4-one (N3); 14-(3,4-Dimethoxy-phenyl)-2,3,10,11- tetramethoxy-7,8-dihydro-5-oxa-6b-aza-benzo[f]naphtho[2,1-α]azulene-6,13-dione (N4); 1-(3,4-Dimethoxy-phenyl)-3-[2-(3,4-dimethoxy-phenyl)-ethyl]-7,8-dimethoxy-4-oxo-3,4-dihydro-5-oxa-3-aza-cyclopenta[α]naphthalene-2-carboxylic acid dimethylamide (N5); and 1-[2-(4-Methoxy-phenyl)-ethyl]-3,4-bis-(3,4,5-trimethoxy-phenyl)-1H-pyrrole-2,5-dicarboxylic acid dimethyl ester (N6).

Chemical Definitions:

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. The term "alkyl" is intended to include aliphatic groups including saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like.

As used herein, the term "nitro" means —$NO_2$; the term "halogen" designates —F, —Cl, —Br or —I; the term "thiol" means SH; and the term "hydroxyl" means —OH.

The term "alicyclic group" includes closed ring structures of three or more carbon atoms. Alicyclic groups include cycloparaffins which are saturated cyclic hydrocarbons, cycloolefins and naphthalenes which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "heterocyclic group" or "heterocycle" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 20 or fewer carbon atoms in its backbone (e.g., $C_1$-$C_{20}$ for straight chain, $C_3$-$C_{20}$ for branched chain), and more preferably 12 or fewer. Likewise, preferred cycloalkyls have from 4-10 carbon atoms in their ring structure, and more preferably have 4-7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, (e.g., phenylmethyl (benzyl)).

The term "alkylamino" as used herein means an alkyl group, as defined herein, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "amino," as used herein, refers to an unsubstituted or substituted moiety of the formula —$NR_aR_b$, in which $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of $R_a$ and $R_b$, is further substituted with an amino group.

As used herein, the term "modulating" means regulating or controlling as necessary, through preventing, eliminating, reducing, maintaining or increasing a desired effect. The desired effect can be an effect on inflammatory cell accumulation and/or proliferation.

An "immune response" refers to a response in a subject elicited by a stimulus, comprising activation of inflammatory cells. "Activation" comprises recruitment of inflammatory cells from the blood to lymphoid and non-lymphoid tissues to the stimulus by a process involving the release of chemokines and other factors that promote adhesion, movement, and/or proliferation of inflammatory cells. As used herein, "proliferation" refers to the expansion, by rapid duplication, of cells.

"Accumulation" of inflammatory cells refers to the build up of inflammatory cells during an immune response. Accumulation can occur, for example, through cell movement and/or proliferation.

A "subject" is a vertebrate, preferably a mammal, more preferably a human. Mammals include, but are not limited to, humans, farm animals, sport animals, and pets.

An "adverse immune response" refers to any immune response having a detrimental effect in a subject. The adverse immune response can be an inflammatory response. An "inflammatory response" is an adverse response that produces inflammation. An inflammatory response can result, for example, from infection, autoimmunity, as well as transplantation and implantation of organs, tissues and synthetic materials that bring about an inflammatory response, but it is not so limited.

"Inflammation," as used herein refers to an adverse immune response characterized by excessive inflammatory cell build up. Inflammation can be caused, for example, by pathogenic infection, irritation or disease. Inflammation can also be caused by autoimmunity, wherein a subject's own antibodies react with host tissue or in which immune effector T cells are autoreactive to endogenous self-peptides and cause destruction of tissue.

An "inflammatory cell" is a cell contributing to an immune response that can include, but is not limited to, smooth muscle cells, follicular dendritic cells, Langerhans cells, interstitial dendritic cells, interdigitating dendritic cells, blood and veiled dendritic cells, leukocytes, lymphocytes (B-lymphocytes and T-lymphocytes), monocytes, macrophages, foam cells, tissue-specific macrophages such as alveolar macrophages, microglia, mesangial cells, histiocytes, and Kupffer cells, neutrophils, basophils, mast cells, natural killer cells, endothelial cells, eosinophils, megakaryocytes, platelets, erythrocytes and polymorphonuclear cells (e.g., granulocytes).

The term "inflamed tissue" can be used to describe any biological tissue that has mounted an immune response to, for example, foreign agents, bacterial, fungal, viral, mycoplasmal, prion, rickettsial, mycobacterial, and other infections, shear stress, or diseases, e.g., granulomatous diseases exemplified by sarcoidosis, tuberculosis, and granulomas, immediate-type and delayed-type hypersensitivity reactions, immune responses from transplantation, and inflammatory diseases.

The term "target site" refers to regions, aggregates, or populations of cells or tissues where an adverse immune response has been mounted, that is, where inflammatory cells accumulate.

"Immunesuppressive activity" refers to the ability of a compound to decrease or eliminate inflammatory cell activation or proliferation.

Additional terms are described in context throughout this disclosure.

II. Compositions and Methods of the Invention

Compositions and methods of the present invention promote immunosupression through reduction or inhibition of inflammatory cell accumulation at a site of inflammation. Immunosupression can bring therapeutic benefit to patients suffering from inflammation.

As used herein, a "therapeutically effective amount" comprises an amount of a ningalin sufficient to decrease an adverse immune response. Therapeutically effective amounts can include about 50 to about 4000 $^{mg}/m^2$ of one or more ningalins per dose.

Ningalins of the invention comprise all members of the ningalin class of marine natural products, which possess a common 3,4-diaryl substituted pyrrole nucleus bearing a 2-carboxyl. Ningalins of the invention include but are not limited to N1, N2, N3, N4, N5, and N6 (FIG. 1), Ningalin A, Ningalin B and analogs thereof.

Ningalins comprise a family of 3,4-dihydroxyphenylalanine (DOPA)-derived o-catechol metabolites that include the tunichromes (Bruening, R. C.; et al. J. Am. Chem. Soc. 1985, 107, 5289; Bruening, R. C.; et al. J. Nat. Prod. 1986, 49, 193; Bayer, E; et al. Angew. Chem. Int. Ed. Engl. 1992, 31, 52; Oltz, E. M.; et al. J. Am. Chem. Soc. 1988, 110, 6162; Ryan, D. E.; et al. J. Am. Chem. Soc. 1992, 114, 9659; Taylor, S. W.; et al. Arch. Biochem. Biophys. 1995, 324, 228). Ningalin A is well described in the art (Boger, D. L. et al., J. Am. Chem. Soc. 1999, 121, 54, the contents of which are incorporated herein by reference). Ningalin B is the second member of the ningalin family (Kang, H.; Fenical, W. J. Org. Chem. 1997, 62, 3254). Ningalin B and related analogs are described in U.S. Application Publication No. 20030220320 and Boger D. L. et al., J. Org. Chem. 2000, 65, 2479, the contents of each which are incorporated herein by reference. N1, N2, N3, N4, N5, and N6 (FIG. 1) were previously described by Boger D. L. et al., J. Org. Chem. 2000, 65, 2479 as N10, N11, N13, N14, N15 and N30, respectively. Other ningalins are referenced in Soenen D. R. et al, Bioorganic and Med. Chem. Letts. 2003, 13, 1777-1781 the contents of which are incorporated herein by reference.

Ningalin analogs of the present invention comprise, for example, analogs having variations in structure, but retaining the essential functional activity of a native ningalin (i.e, the ability to modulate an adverse immune response, such as by decreasing inflammatory cell activation or proliferation). As referred to herein, an analog having "native ningalin activity" possesses a functional ability decrease activation or proliferation of inflammatory cells which is at least equivalent to that of the compound in its native (e.g., unmodified) form. Analogs of the invention may exceed the physiological activity of the compound in its native form. Methods of analog design are well known in the art, and synthesis can be carried out according to such methods by modifying the chemical structure of a native ningalin such that the resultant analogs exhibit equivalent or enhanced function (U.S. Application Publication No. 20030220320). These chemical modifications include, but are not limited to, substituting alternative R groups and varying the degree of saturation at specific carbon atoms of the native molecule. Analogs of the invention can be relatively resistant to in vivo degradation, resulting in a more prolonged therapeutic effect upon administration. Assays for measuring functional activity include, but are not limited to, those described in the Examples below.

In one embodiment, methods of the present invention comprise identifying compounds or compositions that mimic, exceed or increase native ningalin A or B activity, for example, ningalin analogs. Accordingly, methods of the present invention further relate to screening for compounds that mimic or exceed activity of ningalins presently known in the art.

Design of assays (e.g., cell-based assays) to identify compounds effecting or possessing native ningalin activity, is well within the skill in the art. The end point of the assays will typically measure a physiologic effect. The physiologic effect can comprise modulating inflammatory cellular movement and/or proliferation in response to interaction with a specific candidate or composition, referred to herein as a test compound. Preferably, inflammatory cell lines are used in cell-based assays.

In one embodiment, the present invention provides a method of screening ningalin analogs for immunosuppressive activity comprising the steps of:
a) contacting test inflammatory cells with an amount of a ningalin analog sufficient to exert a physiologic effect comprising decreasing inflammatory cell proliferation and measuring the physiologic effect on the test inflammatory cells;
b) contacting control inflammatory cells with a ningalin and measuring the physiologic effect on the control inflammatory cells; and
comparing the physiologic effect of the ningalin analog to the physiologic effect of the ningalin, wherein determination of a physiologic effect of the ningalin analog is expressed relative to that of the ningalin.

Compositions of the present invention are well suited for the preparation of pharmaceutical compositions. The pharmaceutical compositions of the invention can be administered to any subject that may experience the beneficial effects of the compounds of the invention.

The pharmaceutical compositions can be administered by any means that achieve their intended purpose. For example, administration can be by topical, parenteral, subcutaneous, intravenous, intramuscular, intraperitoneal, transdermal, or buccal routes. Alternatively, or concurrently, administration can be by the oral route. The dosage administered will be dependent upon the age, health, and weight of the recipient, kind of concurrent treatment, if any, frequency of treatment and the nature of the effect desired.

In addition to the pharmacologically active compounds, the pharmaceutical preparations can contain suitable pharmaceutically acceptable carriers comprising excipients and auxiliaries that facilitate processing of the active compounds into preparations that can be used pharmaceutically. Preferably, the preparations, particularly those preparations that can be administered orally and that can be used for the preferred type of administration, such as tablets, dragees, and capsules, and also preparations that can be administered rectally, such as suppositories, as well as suitable solutions for administration by injection or orally, contain from about 0.001 to about 99 percent, preferably from about 0.01 to about 95 percent, about 1.0 to about 90 percent, or about 10 to about 50 percent of active compound(s), together with the excipient. Standard texts, such as "Remington's Pharmaceutical Science", 17th edition, 1985, "Hand Book of Pharmaceutical Excipients, $4^{th}$ edition 2003, incorporated herein by reference, may be consulted to prepare suitable preparations, without undue experimentation. Suitable dosages can also be based upon the text herein and documents cited herein.

The dose ranges for the administration of the compositions of the present invention are those large enough to produce the desired effect (without exceeding the maximal tolerated doses) whereby, for example, the adverse immune response is reduced or eliminated or ameliorated. In specific embodiments, from about 50 to about 500 $mg/m^2$, from about 500 to about 1000 $mg/m^2$, from about 1000 to about 2000 $mg/m^2$, and from about 2000 to about 4000 $mg/m^2$ of one or more ningalins per dose is administered. Generally, the dosage will vary with the age, condition, sex, and extent of the disease in the patient. The doses should not be so large as to cause adverse side effects, such as unwanted cross-reactions, anaphylactic reactions, and the like. Counter indications, if any, immune tolerance, and other variables will also affect the proper dosage. The molecules can be administered parenterally by injection or by gradual profusion over time.

The pharmaceutical preparations are manufactured in a manner that is itself known, for example, by means of conventional mixing, granulating, dragee making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropyl-methyl-cellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations that can be used orally include pushfit capsules made of gelatin, as well as soft, sealed capsules made of gelatin and a plasticizer, such as glycerol or sorbitol. The push-fit capsules can contain the active compounds in the form of granules that may be mixed with fillers, such as lactose, binders, such as starches, and/or lubricants, such as talc or magnesium stearate, and, optionally, stabilizers. In soft capsules, the active compounds are preferably dissolved or suspended in suitable liquids, such as fatty oils or liquid paraffin. In addition, stabilizers may be added.

Possible pharmaceutical preparations that can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension including, for example, sodium carboxymethyl cellulose, sorbitol, and/or dextran. Optionally, the suspension may also contain stabilizers.

Additional pharmaceutical methods can be employed to control the duration of action. Delivery systems can include time-release, delayed release or sustained release delivery systems (collectively referred to herein as controlled release). Such systems can avoid repeated administrations of the ningalins, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) difusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. Ningalins can be encapsulated within the aqueous interior and be delivered to cells in an active form (Fraley, et al., Trends Biochem. Sci., (1981) 6:77). In order for a liposome to be an efficient transfer vector, one or more of the following characteristics should be present: (1) encapsulation of the ningalin with high efficiency and retention of biological activity; (2) preferential and substantial binding to a target cell in comparison to non-target cells; and (3) delivery of the aqueous contents of the vesicle to the target cell cytoplasm at high efficiency.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, (1985) 3:235-241.

In one important embodiment, a preferred vehicle is a biocompatible microparticle or implant that is suitable for implantation into the mammalian recipient. Exemplary bioerodible implants that are useful in accordance with this method are described in PCT International Publication No. WO 95/24929, entitled "Polymeric Gene Delivery System" (PCT International application no. PCT/US95/03307). WO 95/24929 describes a biocompatible, preferably biodegradable polymeric matrix for containing an exogenous gene under the control of an appropriate promoter. The polymeric matrix is used to achieve sustained release of the exogenous gene in the patient. In accordance with one embodiment of the invention, the ningalins described herein are encapsulated or dispersed within the biocompatible, preferably biodegradable, polymeric matrix such as that disclosed in WO 95/24929.

The polymeric matrix preferably is in the form of a microparticle such as a microsphere (wherein an agent is dispersed throughout a solid polymeric matrix) or a microcapsule (wherein an agent is stored in the core of a polymeric shell). Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and ningalins are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., Biotech. And Bioeng., (1996) 52:96-101 and Mathiowitz et al., Nature, (1997) 386:410-414.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

Ningalins can be delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules, (1993) 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr., et al., Nature, 1999, 397:335-338, the contents of which are expressly incorporated herein by reference.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above. In certain embodiments, the agents of the invention are delivered directly to the site at which there is inflammation, e.g., the joints in the case of a subject with rheumatoid arthritis, the blood vessels of an atherosclerotic organ, etc. For example, this can be accomplished by attaching a ningalin to the surface of a balloon catheter; inserting the catheter into the subject until the balloon portion is located at the site of inflammation, e.g. an atherosclerotic vessel, and inflating the balloon to contact the balloon surface with the vessel wall at the site of the occlusion. In this manner, the compositions can be targeted locally to particular inflammatory sites to modulate immune cell migration to these sites. In another example the local administration involves an implantable pump to the site in need of such treatment. Preferred pumps are as described above. In a further example, when the treatment of an abscess is involved, the ningalins may be delivered topically, e.g., in an ointment/dermal formulation. Optionally, the agents are delivered in combination with other therapeutic agents (e.g., anti-inflammatory agents, immunosuppressant agents, etc.). Quantitative determination of synergism or antagonism is carried out with computerized analysis using the classic isobologram and the combination index of Chou and Taklay, Advances in Enzyme Regulation, 1984, 22, 27.

The preclinical and clinical therapeutic use of the compositions and methods of the present invention to ameliorate acute and chronic inflammatory disorders will be best accomplished by those of skill, employing accepted principles of diagnosis and treatment. Such principles are known in the art, and are set forth, for example, in Petersdorf, R. G. (1983).

Compositions and methods of the present invention are useful for treating a number of disorders associated with adverse immune responses (e.g., from exposure to an allergen or pathogen or transplantation of heterologous blood, organ or tissue).

Immune rejection is a major problem confronting organ transplantation. The principal approach to mitigate rejection is the pharmacological suppression of the immune system of an organ recipient. Methods of the invention further provide a means whereby the rejection of tissue or organs after transplantation can be prevented or controlled, thus prolonging the survival of the tissue or organ. Commonly transplanted organs include, but are not limited to, kidney, pancreas, liver, heart, intestines, lung, and bone marrow, as allograft or autologous compositions. Accordingly, immunosuppressive ningalin compositions of the present invention can be used to prevent or treat hyperacute, acute and chronic rejection of tissue (including blood) or organs.

Inflammation can be caused by an immune response against "non-self-antigens" (including antigens of necrotic self-material), and the subject in need of treatment according to the invention is a transplant recipient. This is because after tissue (or organ) transplantation, certain antigens from the transplanted material can stimulate the production of immune lymphocytes and/or autoantibodies, which later participate in inflammation/rejection causing inflammation and aggravating the condition (Johnson et al., *Sem. Nuc. Med.* 1989, 19:238; Leinonen et al., *Microbiol. Path.,* 1990, 9:67; Montalban et al., *Stroke,* 1991, 22:750).

Accordingly, immunosuppressive ningalins can be used in transplant settings, where cells or tissues to be transplanted can be treated prior to transplant into a subject in order to reduce the likelihood of rejection or graft-versus-host disease (GVHD). Similarly, ningalins can be used to tolerize the immune system to an antigen that it would otherwise mount an immune response against, by administration prior to, simultaneously with or post transplantation.

Immunosuppressive agents often exert their effect by inhibiting the action of lymphokines; an important example is the capacity of cyclosporine to suppress the synthesis of interleukin-2 by inflammatory cells. In addition to their capacity to suppress the formation of eicosanoids, the glucocorticoids and some other compounds produce their anti-inflammatory and immunosuppressive effects by inhibiting the synthesis and action of several cytokines produced by inflammatory cells. Compounds such as histamine, bradykinin, 5-hydroxy-tryptamine, prostaglandins and platelet-activating factor are known to be triggers of the inflammation processes. Without being bound by theory, it is believed that ningalins inhibit the activation and/or proliferation of inflammatory cells in response to these, or other stimuli.

Combinations of drugs and treatment regimens are also contemplated by the invention. The ningalins of the invention can be administered alone or in combination with other therapeutic drugs, including those used in connection with organ rejection therapy and particularly including an immunosupressant. Specifically, ningalins may be administered with one or more drugs including, but not limited to adrenocorticosteroids, cyclosporin, tacrolimus (FK506), sirolimus (rapamycin), sulfasalazine, methoxsalen, methotrexate, mycophenolic acid (mycophenolate mofetil), everolimus, azathiprine, steroids and NOX-100. Administration regimens are described by "Immunosuppressive Agents" in Goodman & Gilman's "The pharmacological basis of therapeutics" 9th Ed. (Hardman et al. eds) McGraw-Hill pp. 1264-1275 and the Physician's Desk Reference 58$^{th}$ Ed., Thompson.

According to another embodiment, the invention provides compositions and methods that suppress inflammation arising from a implantation or transplantation of a material surface. Such methods involve ex vivo coating or loading material surfaces with one or more of the immunosuppressive ningalins provided herein. "Material surfaces" as used herein, include, but are not limited to, dental and orthopedic prosthetic implants, artificial valves, stents and organic implantable tissue such as an autologous, heterologous, allogeneic, or xenogenic tissue or organ or graft thereof.

Implantable prosthetic devices have been used in the surgical repair or replacement of internal tissue for many years. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic and dental implants use high performance metals such as cobalt-chrome and titanium alloy to achieve high strength. These materials are readily fabricated into the complex shapes typical of these devices using mature metal working techniques including casting and machining.

The material surface is coated with an amount of ningalin that can vary depending upon the desired therapeutic effect. In important embodiments, the material surface is part of an implant. In important embodiments, the material surface may also be coated with a cell growth potentiating agent, an anti-infective agent, and/or an anti-inflammatory agent.

Within the scope of the invention, an adverse immune response can comprise an inflammatory response, but it is not so limited. The inflammatory response can be attributed to various diseases and conditions that affect one or more organs or organ systems including, but not Invited to, the peripheral nervous system, hematological system, bone marrow, the central nervous system, skin, appendix, gastrointestinal tract (including but not limited to esophagus, duodenum, and colon), respiratory/pulmonary system (including but not limited to lung, nose, pharynx, larynx), eye, genito-reproductive system, gums, liver/biliary ductal system, renal system (including but not limited to kidneys, urinary tract, bladder), connective tissue (including but not limited to joints, cartilage), cardiovascular system, muscle, heart, spleen, breast, lymphatic system, ear, endocrine/exocrine system (including but not limited to lacrimal glands, salivary glands, thyroid gland, pancreas), and bone/skeletal system.

Inflammatory diseases that affect the peripheral nervous system include, but are not limited to, radiculitis. Inflammatory diseases of the central nervous system include acute hemorrhagic leukoencephalitis, cholesterol granuloma, meningoencephalitis, optic neuritis, and Parsonage-Aldren-Turner syndrome, but are not limited to these diseases. Inflammatory diseases of the skin can include, but are not limited to, acute infantile hemorrhagic edema, contact dermatitis, Favre-Racouchot syndrome, folliculitis, panniculitis, Riehl's melanosis, Stevens-Johnson syndrome, and trichostasis spinulosa. Inflammatory diseases of the appendix include appendicitis.

Atrophic gastritis, Barrett's esophagus, Celiac disease, colitis, colonic diverticulitis, Curling's ulcers, Cushing's ulcers, esophagitis, phlegmonous gastritis, proctitis, toxic megacolon, and typhlitis are some inflammatory diseases that affect the gastrointestinal tract. Inflammatory diseases of the respiratory/pulmonary system include, but are not limited to atrophic rhinitis, bronchiolitis obliterans organizing pneumonitis, pleural empyema, endogenous lipoid pneumonia, laryngeal granuloma, lymphocytic interstitial pneumonia, pharyngitis, pleuritis, sinusistis, and sterile pneumonitis. Inflammatory diseases of the eye can be blepharitis, dacryocystitis, endophthalmitis, Fuch's heterochromic cyclitis, giant papillary conjunctivitis, optic neuritis, phlyctenular keratoconjunctivitis, scleritis, but are not limited to these examples.

The allergic reaction has been extensively studied and the basic immune mechanisms involved are well known.

Diseases characterized by inflammation that affect the genito-reproductive system include, but are not limited to Bowenoid papulosis, cervicitis, cystitis, epidydymo-orchitis, peritonitis, and prostatitis. Inflammatory diseases that affect the gums include cancrum oris, giant cell granuloma, gingivitis, pericoronitis, periodontitis, and pulpitis, but are not limited to these examples. Diseases states that are characterized by inflammation and that affect the liver/biliary ductal system include, but are not limited to, cholangitis and perihepatitis. Inflammatory diseases of the renal system can include chronic interstitial nephritis, Hunner's ulcer, post-streptococcal glomerulonephritis, and xanthogranulomatous pyelonephritis. Disease states that affect connective tissue include, but are not limited to, De Quervain's tenosynovitis, pyrophosphate arthropathy, reactive arthropathy, sacroilitis, synovitis, tenosynovitis, Tietze's costochondritis, and urate crystal arthropathy.

Disease states characterized by inflammation of the cardiovascular system include endocarditis, pericarditis, thrombophlebitis, and vasculitis, but are not limited to these examples. Inflammatory disease states that affect muscle include but are not limited to, myositis and Parsonage-Aldren-Turner syndrome. Mastitis and Mondor's disease of the breast are some inflammatory conditions that affect the breast. Diseases of the lymphatic system that are characterized by inflammation include mesenteric adenitis and pseudolymphoma, but are not limited to these examples. Inflammatory diseases of the ear can include diseases such as myringitis bullosa. Inflammatory diseases of the endocrine/exocrine system can include necrotizing sialometaplasia, pancreatitis, parotitis, and thyroiditis, while diseases of the bone/skeletal system characterized by inflammation include osteitis, osteitis fibrosa cystica, osteitis pubis, and periostitis, but are not limited to these examples. It is evident that many inflammatory diseases can be systemic and affect more than one organ system. Some systemic inflammatory diseases can include gangrene, Jarisch-Herxheimer reaction, and Reiter's syndrome.

Methods and compositions of the invention are also suitable for modulation of adverse responses comprising autoimmune responses. Autoimmune disease is a class of diseases in which a subject's own antibodies react with host tissue or in which immune effector T cells are autoreactive to endogenous self-peptides and cause destruction of tissue. Autoimmune diseases include, but are not limited to, acquired factor VIII deficiency, acquired generalized lipodystrophy, alopecia areata, ankylosing spondylitis, anticardiolipin syndrome, autoimmune adrenalitis, autoimmune neutropenia, autoimmune oophoritis, autoimmune orchitis, autoimmune polyendocrine syndrome type 2, autoimmune sclerosing pancreatitis, Balanatis xerotica obliterans, Behcet's disease, benign recurrent meningitis, Calcinosis-Raynaud's sclerodactyly-telangiectasia syndrome, Caplan's disease, Churg-Strauss syndrome, cicatricial pemphigoid, Degos' disease, dermatitis herpetiformis, discoid lupus erythematosus, Dressler's syndrome, Eaton-Lambert syndrome, eosinophilic fasciitis, eosinophilic pustular folliculitis, epidermolysis bullosa acquisita, Evans syndrome, cryptogenic fibrosing alveolitis, Henoch-Schönlein purpura, Hughes-Stovin syndrome, hypertrophic pulmonary osteo-arthropathy, autoimmune hypoparathyroidism, inclusion body myosins, inflammatory bowel disease, insulin antibodies, insulin receptor antibodies, juvenile chronic arthritis, Kawasaki disease, linear IgA disease, lymphocytic mastisis, microscopic polyangiitis, Mikulicz's syndrome, Miller-Fisher syndrome, morphoea, acquired neuromyotonia, oculovestibuloauditory syndrome, paraneoplastic pemphigus, paroxysmal cold hemoglobinuria, partial lipodystrophy, polyarteritis nodosa, polychondritis, polymyalgia rheumatica, polyradiculoneuropathy, postpartum thyroiditis, primary biliary cirrhosis, primary sclerosing cholangitis, pyoderma gangrenosum, rhizomelic pseudopolyarthritis, sarcoidosis, Sicca syndrome, Sneddon-Wilkinson disease, Still's Disease, Susac's syndrome, sympathetic ophthalmitis, systemic sclerosis, Takayasu's arteritis, temporal arteritis, thrombangiitis obliterans, ulcerative colitis, vitiligo, Vogt-Koyanagi-Harada syndrome, Wegener's granulomatosis, rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Graves' disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, insulin-dependent diabetes mellitus, graft versus host disease, uveitis, rheumatic fever, Guillain-Barre syndrome, psoriasis, and autoimmune hepatitis.

In other embodiments, the adverse immune response results from exposure to allergens. The generic name for molecules that cause an allergic reaction is allergen. There are numerous species of allergens. The allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

The symptoms of the allergic reaction vary, depending on the location within the body where the IgE reacts with the antigen. If the reaction occurs along the respiratory epithelium the symptoms are sneezing, coughing and asthmatic reactions. If the interaction occurs in the digestive tract, as in the case of food allergies, abdominal pain and diarrhea are common. Systematic reactions, for example following a bee sting, can be severe and often life threatening.

Delayed type hypersensitivity, also known as type IV allergy reaction is an allergic reaction characterized by a delay period of at least 12 hours from invasion of the antigen into the allergic subject until appearance of the inflammatory or immune reaction. The T lymphocytes (sensitized T lymphocytes) of individuals in an allergic condition react with the antigen, triggering the T lymphocytes to release lymphokines (macrophage migration inhibitory factor (MIF), macrophage activating factor (MAF), mitogenic factor (MF), skin-reactive factor (SRF), chemotactic factor, neovascularization-accelerating factor, etc.), which function as inflammation mediators, and the biological activity of these lymphokines, together with the direct and indirect effects of locally appearing lymphocytes and other inflammatory immune cells, give rise to the type IV allergy reaction. Delayed allergy reactions include tuberculin type reaction, homograft rejection reaction, cell-dependent type protective reaction, contact dermatitis hypersensitivity reaction, and the like, which are known to be most strongly suppressed by steroidal agents. Consequently, steroidal agents are effective against diseases which are caused by delayed allergy reactions. Long-term use of steroidal agents at concentrations currently being used can, however, lead to the serious side-effect known as steroid dependence. The methods of the invention solve some of these problems, by providing for lower and fewer doses to be administered.

Allergic conditions or diseases in humans include but are not limited to eczema, allergic rhinitis or coryza, hay fever, conjunctivitis, bronchial or allergic asthma, urticaria (hives) and food allergies; atopic dermatitis; anaphylaxis; drug allergy; angioedema; and allergic conjunctivitis. Allergic diseases in dogs include but are not limited to seasonal dermatitis; perennial dermatitis; rhinitis: conjunctivitis; allergic asthma; and drug reactions. Allergic diseases in cats include but are not limited to dermatitis and respiratory disorders; and food allergens. Allergic diseases in horses include but are not limited to respiratory disorders such as "heaves" and dermatitis. Allergic diseases in non-human primates include but are not limited to allergic asthma and allergic dermatitis.

Immediate immune hypersensitivity (or anaphylactic response) is a form of allergic reaction which develops very quickly, i.e. within seconds or minutes of exposure of the patient to the causative allergen, and it is mediated by IgE antibodies made by B lymphocytes. In nonallergic patients, there is no IgE antibody of clinical relevance; but, in a person suffering with allergic diseases, IgE antibody mediates immediate hypersensitivity by sensitizing mast cells which are abundant in the skin, lymphoid organs, in the membranes of the eye, nose and mouth, and in the respiratory tract and intestines.

Mast cells have surface receptors for IgE, and the IgE antibodies in allergy-suffering patients become bound to them. As discussed briefly above, when the bound IgE is subsequently contacted by the appropriate allergen, the mast cell is caused to degranulate and to release various substances called bioactive mediators, such as histamine, into the surrounding tissue. It is the biologic activity of these substances which is responsible for the clinical symptoms typical of immediate hypersensitivity; namely, contraction of smooth muscle in the airways or the intestine, the dilation of small blood vessels and the increase in their permeability to water and plasma proteins, the secretion of thick sticky mucus, and in the skin, redness, swelling and the stimulation of nerve endings that results in itching or pain.

Many allergies are caused by IgE antibody generation against harmless allergens.

The types of antibodies associated with a Th1 response are generally more protective because they have high neutralization and opsonization capabilities. Th2 responses involve predominately antibodies and these have less protective effect against infection and some Th2 isotypes (e.g., IgE) are associated with allergy. Strongly polarized Th1 and Th2 responses not only play different roles in protection, they can promote different immunopathological reactions. Th1-type responses are involved organ specific autoimmunity such as experimental autoimmune uveoretinitis (Dubey et al, 1991, Eur Cytokine Network 2: 147-152), experimental autoimmune encephalitis (EAE) (Beraud et al, 1991, Cell Immunol 133: 379-389) and insulin dependent diabetes mellitus (Hahn et al, 1987, Eur. J. Immunol. 18: 2037-2042), in contact dermatitis (Kapsenberg et al, Immunol Today 12: 392-395), and in some chronic inflammatory disorders. In contrast Th2-type responses are responsible for triggering allergic atopic disorders (against common environmental allergens) such as allergic asthma (Walker et al, 1992, Am Rev Resp Dis 148: 109-115) and atopic dermatitis (van der Heijden et al, 1991, J Invest Derm 97: 389-394), are thought to exacerbate infection with tissue-dwelling protozoa such as helminths (Finkelman et al, 1991, Immunoparasitol Today 12: A62-66) and *Leishmania major* (Caceres-Dittmar et al, 1993, Clin Exp Immunol 91: 500-505), are preferentially induced in certain primary immunodeficiencies such as hyper-IgE syndrome (Del Prete et al, 1989, J Clin Invest 84: 1830-1835) and Omenn's syndrome (Schandene et al, 1993, Eur J Immunol 23: 56-60), and are associated with reduced ability to suppress HIV replication (Barker et al, 1995, Proc Soc Nat Acad Sci USA 92: 11135-11139).

Thus, in general, it appears that allergic diseases are mediated by Th2 type immune responses. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation, and mast cell growth. Th1 cytokines, especially IFN-g and IL-12, can suppress the formation of Th2 clones and production of Th2 cytokines.

An "allergen" as used herein is a molecule capable of provoking an immune response characterized by production of IgE. Thus, in the context of this invention, the term allergen means a specific type of antigen which can trigger an allergic response which is mediated by IgE antibody. The method and preparations of this invention extend to a broad class of such allergens and fragments of allergens or haptens acting as allergens. Allergens include but are not limited to Environmental Aeroallergens; plant pollens such as Ragweed/hayfever; Weed pollen allergens; Grass pollen allergens; Johnson grass; Tree pollen allergens; Ryegrass; House dust mite allergens; Storage mite allergens; Japanese cedar pollen/hay fever Mold spore allergens; Animal allergens (cat, dog, guinea pig, hamster, gerbil, rat, mouse); Food Allergens (e.g., Crustaceans; nuts, such as peanuts; citrus fruits); Insect Allergens (Other than mites listed above); Venoms: (Hymenoptera, yellow jacket, honey bee, wasp, hornet, fire ant); Other environmental insect allergens from cockroaches, fleas, mosquitoes, etc.; Bacteria such as streptococcal antigens; Parasites such as Ascaris antigen; Viral Antigens; Fungal spores; Drug Allergens; Antibiotics; penicillins and related compounds; other antibiotics; Whole Proteins such as hormones (insulin), enzymes (Streptokinase); all drugs and their metabolites capable of acting as incomplete antigens or haptens; Industrial Chemicals and metabolites capable of acting as haptens and stimulating the immune system (Examples are the acid anhydrides (such as trimellitic anhydride) and the isocyanates (such as toluene diisocyanate)); Occupational Allergens such as flour (ie. Baker's asthma), castor bean, coffee bean, and industrial chemicals described above; flea allergens; and human proteins in non-human animals.

Allergens include but are not limited to cells, cell extracts, proteins, polypeptides, peptides, polysaccharides, polysaccharide conjugates, peptide and non-peptide mimics of polysaccharides and other molecules, small molecules, lipids, glycolipids, and carbohydrates. Many allergens, however, are protein or polypeptide in nature, as proteins and polypeptides are generally more antigenic than carbohydrates or fats.

Examples of specific natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g.

*Phalaris arundinacea*); *Paspalum* (e.g. *Paspalum notatum*); *Sorghum* (e.g. *Sorghum halepensis*); and *Bromus* (e.g. *Bromus inermis*).

In other embodiments, the adverse immune response results from exposure to pathogens. Pathogens include, for example, viruses, bacteria, parasites, and fungi.

Examples of viruses that have been found in humans include but are not limited to: Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris*, *Borelia burgdorferi*, *Legionella pneumophilia*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus influenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Examples of fungi include *Cryptococcus neoformans*, *Histoplasma capsulatum*, *Coccidioides immitis*, *Blastomyces dermatitidis*, *Chlamydia trachomatis*, *Candida albicans*.

Other infectious organisms (i.e., protists) include *Plasmodium* spp. such as *Plasmodium falciparum*, *Plasmodium malariae*, *Plasmodium ovale*, and *Plasmodium vivax* and *Toxoplasma gondii*. Blood-borne and/or tissues parasites include *Plasmodium* spp., *Babesia microti*, *Babesia divergens*, *Leishmania tropica*, *Leishmania* spp., *Leishmania braziliensis*, *Leishmania donovani*, *Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

The following examples are provided as a further description of the invention, and to illustrate but not limit the invention.

EXAMPLES

Example 1

Immune Suppression in Tumor Bearing Mice

Drug studies using N3 (20 mg/Kg) against P388/DX tumors in $B6D2F_1$ mice were performed as follows. $B6D_2F_1$ mice (three mice per group) were implanted intraperitoneal ("i.p.") on day 0 with $10^6$ P388/DX leukemic cells resistant to Adriamycin (Doxorubicin). Drug exposure started 6 hours later with saline (i.p., control); N3 (20 mg/kg, i.p.); Adriamycin (1.5 mg/kg and 3.0 mg/kg, iv.); the combination of N3 (20 mg/kg, i.p.) and Adriamycin (1.5 mg/kg, i.v.) or the combination of N3 (20 mg/kg, ip.) and Adriamycin (3.0 mg/kg, i.v.) daily for three days. This experiment was originally designed to demonstrate the enhanced chemotherapeutic effect of Adriamycin when used in combination with N3. Surprisingly, it was discovered that treatment with N3 alone not only failed to increase the lifespan of tumor bearing $B6D_2F_1$ mice, but instead, decreased the lifespan by 12% as shown in Table 1. This data indicated that N3 had an immunosuppressive effect on the immunocompetent $B6D_2F_1$ mice, which caused the P388/DX leukemia to progress faster than in the untreated control group.

TABLE 1

| Group | Dosage (mg/kg) | Route | Schedule | Median survival time (days ± SD) | Lifespan increase (%) | Lifespan increase (days) | Log cell kill* |
|---|---|---|---|---|---|---|---|
| Control | 0 | | | 10.5 ± 0.66 | 0 | 0 | |
| N3 | 20 | Ip | QD × 3 | 9.25 ± 0.66 | −12 | −1.25 | |
| Adriamycin | 1.5 | Iv | QD × 3 | 11.25 ± 1.75 | +7 | +0.75 | 0.56 |
| Adriamycin + N3 | Adr. - 1.5 N3 - 20 | Adr. iv N3 ip | QD × 3 | 13.67 ± 0.52 | +30 | +3.17 | 2.39 |
| Adriamycin | 3.0 | Iv | QD × 3 | 12.08 ± 1.81 | +15 | +1.58 | 1.19 |
| Adriamycin + N3 | Adr. - 3.0 N3 - 20 | Adr. iv N3 ip | QD × 3 | 13.00 ± 0.71 | +24 | +2.50 | 1.88 |

*Calculated assuming doubling time is 0.4 day (9.6 hr).

B6D$_2$F$_1$ mice (four mice per group) were implanted i.p. on day 0 with 10$^6$ P388/DX leukemic cells. Treatment started 6 hours later with saline i.p. (control); N3 (20 mg/kg, i.p.); paclitaxel (Taxol®, 5 mg/kg and 10 mg/kg, i.v.); and the combination of N3 (20 mg/kg, i.p.) and Taxol (5 mg/kg, i.v.) or N3 (20 mg/kg, i.p.) and Taxol (10 mg/kg, iv.), daily for three days. This experiment was also originally designed to demonstrate the enhanced chemotherapeutic effect of Taxol when used in combination with N3. Treatment with N3 again decreased the lifespan of tumor bearing mice compared to saline treated controls (Table 2).

TABLE 2

| Group | Dosage (mg/kg) | Route | Schedule | Median survival time (days ± SD) | Lifespan increase (%) | Lifespan increase (days) | Log cell kill* |
|---|---|---|---|---|---|---|---|
| Control | 0 | | | 9.19 ± 1.30 | 0 | 0 | |
| N3 | 20 | ip | QD × 3 | 8.00 ± 0.54 | −13 | −1.19 | |
| Taxol | 5.0 | iv | QD × 3 | 9.56 ± 0.62 | +4 | +0.37 | 0.28 |
| Taxol + N3 | Taxol - 5.0 N3 - 20 | Taxol iv N3 ip | QD × 3 | 10.50 ± 1.55 | +14 | +1.31 | 0.99 |
| Taxol | 10.0 | iv | QD × 3 | 9.56 ± 0.88 | +4 | +0.37 | 0.28 |
| Taxol + N3 | Taxol - 10.0 N3 - 20 | Taxol iv N3 ip | QD × 3 | 12.67 ± 1.63† | +38 | +3.48 | 2.62 |

*Calculated assuming doubling time is 0.4 day (9.6 hr).
†One out of four mice died of drug combination toxicity on day 4.

Example 2

Ningalins Suppress Phytostigma Stimulation of Human Lymphocyte Proliferation

To further evaluate the immunosuppressive effect of ningalins, inhibition of lymphocyte proliferation by N3, N5 and N6 was investigated. Phytohemagglutinin (phytostigma or "PHA") induces proliferation of human lymphocytes. [$^3$H] Thymidine incorporation into DNA was determined as a measure of lymphocyte proliferation (Chou T.-C. et al. *Cancer Res.* 37: 3561-3570, 1977). The IC$_{50}$s for immunosuppressive effect (in μM) and the IC$_{50}$s for cytotoxicity (in μM) for N3, N5, and N6 were determined as shown in Table 3. It was determined that ningalins suppress phytostigma stimulation of human lymphocyte proliferation.

Figure 2:
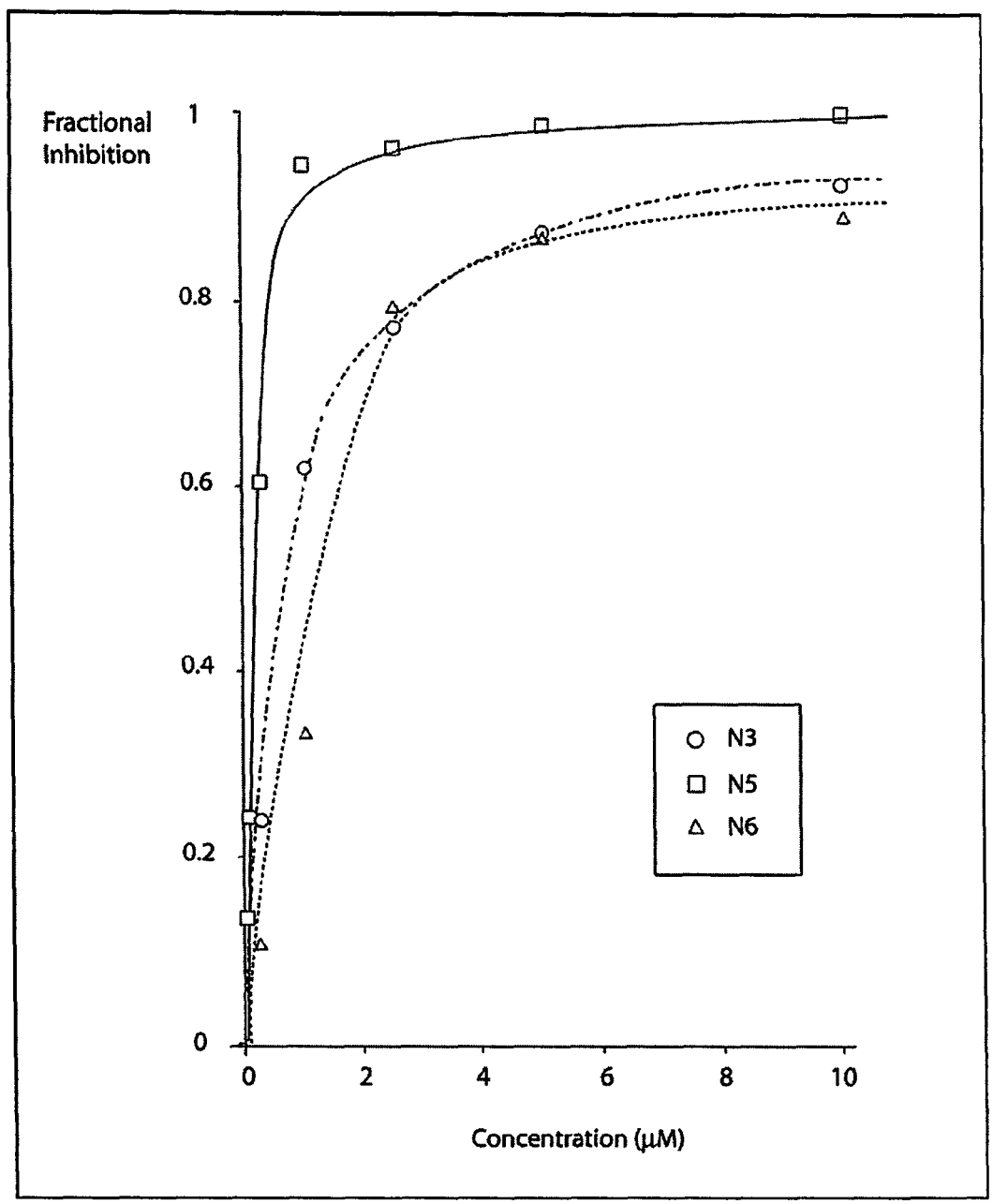
FIG. 2 depicts the dose-effect curves of N3, N5 and N6 on the inhibition of PHA-stimulated lymphocyte proliferation.

The dose-effect curves of N3, N5 and N6 on the inhibition of PHA-stimulated lymphocyte proliferation are shown in FIG. 2. For comparison, the results of a known multi-drug resistance (MDR)-reversing agent, Verapamil, and of a known immunosuppressive agent, cyclosporin A are also shown. As indicated in Table 3, the immunosuppressive effects of ningalins occurred at much lower concentrations than the cytotoxic concentrations as measured by the cell proliferation inhibition. These results indicate that ningalins have selective immunosuppressive effects at non-toxic concentrations.

TABLE 3

| Compound | Cytotoxicity (IC$_{50}$ in μM) [A] | Immunosuppressive Effect (IC$_{50}$ in μM) [B] | Selectivity Ratio [A]/[B] |
|---|---|---|---|
| Ningalin-3 (N3) | 51.3 ± 18.0 | 0.51 ± 0.19 | 100.6 |
| Ningalin-5 (N5) | 17.1 ± 4.6 | 0.17 ± 0.01 | 100.3 |

TABLE 3-continued

| Compound | Cytotoxicity (IC$_{50}$ in μM) [A] | Immunosuppressive Effect (IC$_{50}$ in μM) [B] | Selectivity Ratio [A]/[B] |
|---|---|---|---|
| Ningalin-6 (N6) | 70.2 ± 20.5 | 1.61 ± 0.31 | 43.6 |
| Verapamil | 188.4 ± 107.2 | 6.90 ± 1.01 | 27.3 |
| Cyclosporine A (C$_s$A) | 6.6 ± 3.1 | 0.102 ± 0.026 | 64.7 |

Example 3

Immunosuppressive Effect of Ningalin 5 ("N5") in Organ Transplantation

Organ transplant experiments were carried out at University of Texas Health Center in Houston, Department of Surgery/Organ Transplant. In all experiments, N5 was dissolved in DMSO (dimethylsulfoxide).

Methods of Heart Transplantation.

Heterotopic heart transplantation was performed in rats and mice. In brief, heart transplantation was performed by previously described modified method. Hearts harvested from donors were perfused with chilled saline and immediately transplanted to recipients under full anesthesia. Suture 10-0 in rats and 12-0 in mice (Ethicon; Somerville, N.J.) was used to perform anastomosis of aorta to aorta and pulmonary artery to vena cava. Heartbeat was evaluated daily and the day of complete cessation was considered rejection. Animals that died within three days after transplantation were excluded from the analysis (less than 5%).

Heart Transplant in Rats

Rat ACI (RT1*) recipients of Lewis (LEW; RT1$^1$) heart allografts were untreated or were treated for 7 days by daily (QDx7) i.p. injections with 20 mg/kg N5. Untreated recipients rejected heart allografts in a mean survival time (MST) of 8.40±0.55 (n=5). In contrast, recipients treated with N5 showed extended allograft survival to a MST of 18.67±2.52 days, which increased life span 122% (n=3; p<0.01). These results document that N5 therapy inhibits rejection of heart allografts in rats.

Heart Transplant in Mice

Mice were also transplanted with heart allografts. In particular, untreated Balb/c (H-2$^d$) recipients rejected C57BL/6 (H-2$^b$) heart allografts at a MST of 7.8±0.84 days (n=5). Treatment with 40 mg/kg N5, QDx7, extended heart allograft survival to 13.33±2.52 days, which increased life span 71%

(n=3; p<0.03). These results confirmed that N5 inhibits rejection of heart allografts in mice.

Methods of Kidney Transplantation

Orthotopic kidney transplantation was performed in rats. In particular, the left kidney of donor was perfused through the aorta with heparinized saline (4° C.) and then harvested after the renal artery, renal vein, and ureter were cut off. End-to-end anastomosis of donor and recipient renal arteries and veins were performed using 10-0 nylon suture (Ethicon; Somerville, N.J.). The recipients' native kidneys were removed on the day of transplantation. Animals that died within three days after transplantation were excluded from the analysis (less than 5%).

Kidney Transplantation in Rats

The effect of N5 (administered in DMSO, 20 mg/kg, i.p. QDx7) on kidney allograft survival was examined. Although untreated ACI recipients acutely rejected LEW kidney allografts at 8.8±0.75 days, a 7-day i.p. daily treatment extended survivals to 26.50±2.12 days, which increased lifespan 200% (n=2; p<0.03). These results document that N5 therapy inhibits rejection of kidney allografts in rats.

TABLE 4

| Animals | Model | Organ | N5 mg/kg | Survival days | MST ± SD days | P* |
|---|---|---|---|---|---|---|
| Rats | LEW ⇒ LEW | heart | — | 8, 8, 9, 9, 9 | 8.40 ± 0.55 | — |
|  | LEW ⇒ LEW | heart | 20 | 18, 19, 21 | 18.67 ± 2.5 | <0.01 |
|  | LEW ⇒ LEW | kidney | — | 8, 8, 9, 9, 9, 10 | 8.83 ± 0.75 | — |
|  | LEW ⇒ LEW | kidney | 20 | 26, 28 | 26.50 ± 2.12 | <0.03 |
| Mice | B6 ⇒ Balb/c | heart | — | 7, 7, 8, 8, 9 | 7.80 ± 075 | — |
|  | B6 ⇒ Balb/c | heart | 40 | 11, 13, 16 | 13.35 ± 2.52 | <0.03 |

*t-test, non-paired, one tail.

Example 4

Immunosuppressive Effect of Ningalin 3 ("N3") in Organ Transplantation

Heart Transplant in Mice

Mice heart allografts were treated with 20 mg/kg of N3, QDx7, i.p. In particular, untreated Balb/c (H-$2^d$) recipients rejected C57BL/6 (H-$2^d$) heart allografts at a MST of 7.80-4.84 days (n=5). Treatment with 20 mg/kg of N3 (i.e., one-half of dose of N5) extended heart allograft survival to 18.75±3.86 days (n=4; p<0.0005), an increase in lifespan of 140%. These results document that N3 therapy inhibits rejection of heart allografts in mice (Table 5).

TABLE 5

| Animals | Model | Organ | N3 mg/kg | Survival days | MST ± SD days | P |
|---|---|---|---|---|---|---|
| Mice | B6 ⇒ Balb/c | Heart | 20 | 19, 24, 15, 17 | 18.75 ± 3.86 | <0.005 |
| Mice | B6 → Balb/c | Heart | — | 7, 7, 8, 8, 9 | 7.80 ± 0.84 | <0.005 |

*t-test, non-paired, one tail.

Example 5

Anti-Inflammatory Effect of Ningalins Against Carrageenan-Induced Paw Edema

Carrageene (1%, 30 μl) was injected i.m. into the pedis of $B6D2F_1$ mice (4 mice/group) to induced edemic inflammation at 0 hours. N3, N5 (i.p. injection) or oral administration of aspirin 500 mg/kg, or topical application of hydrocortisone cream (1%) or Lidex cream (0.05%) to the pedis skins were given at −1, 6, 12 and 24 hours. The control mice received dimethylsulfoxide (the vehicle of ningalins). The pedis areas (in $mm^2$) were measured at 0, 3, 6, 12, 24, 36 and 48 hours.

TABLE 6

| Control Pedis Area $mm^2$ | 0 hr | 3 hr | 6 hr | 12 hr | 24 hr | 36 hr | 48 hr |
|---|---|---|---|---|---|---|---|
| 1 | 11 | 15.1 | 17.4 | 17.5 | 17.2 | 16.6 | 15.7 |
| 2 | 10.5 | 14.9 | 16 | 16.2 | 16.3 | 15.7 | 15.6 |
| 3 | 10.3 | 15.9 | 17.1 | 18.1 | 17.8 | 17.4 | 16.3 |
| 4 | 13.1 | 15.9 | 17.6 | 17.8 | 17.5 | 17.3 | 15.9 |
| Mean | 11.2 | 15.5 | 17 | 17.4 | 17.2 | 16.8 | 15.9 |
| SD | 1.3 | 0.5 | 0.7 | 0.8 | 0.6 | 0.8 | 0.3 |
| SE | 0.7 | 0.3 | 0.4 | 0.4 | 0.3 | 0.4 | 0.2 |

TABLE 7

| Aspirin Pedis Area $mm^2$ | 0 hr | 3 hr | 6 hr | 12 hr | 24 hr | 36 hr | 48 hr |
|---|---|---|---|---|---|---|---|
| 1 | 100 | 142.2 | 151.4 | 138.5 | 116.5 | 114.7 | 118.3 |
| 2 | 100 | 130.5 | 139.8 | 135.6 | 116.9 | 107.6 | 105.9 |
| 3 | 100 | 122 | 124.6 | 120.3 | 108.5 | 94.1 | 92.4 |
| 4 | 100 | 134.5 | 149.6 | 138.9 | 118.6 | 109.7 | 111.5 |
| Mean | 100 | 132.3 | 141.4 | 133.3 | 115.1 | 106.5 | 107 |
| SD | 0 | 8.4 | 12.3 | 8.8 | 4.7 | 10.5 | 13 |
| SE | 0 | 4.2 | 6.2 | 4.4 | 2.7 | 6.1 | 6.5 |

TABLE 8

| N3 Pedis Area $mm^2$ | 0 hr | 3 hr | 6 hr | 12 hr | 24 hr | 36 hr | 48 hr |
|---|---|---|---|---|---|---|---|
| 1 | 100 | 134.4 | 140.6 | 140.6 | 134.4 | 131.1 | 131.1 |
| 2 | 100 | 142.7 | 159.2 | 150.5 | 142.7 | 136.9 | 136.9 |
| 3 | 100 | 141.7 | 153.4 | 139.8 | 136.9 | 121.9 | 115.8 |
| 4 | 100 | 139.5 | 151.8 | 135.1 | 128.1 | 127.9 | 126 |
| Mean | 100 | 139.6 | 151.3 | 141.5 | 135.5 | 129.5 | 127.5 |
| SD | 0 | 3.7 | 7.8 | 6.5 | 6 | 6.3 | 9 |
| SE | 0 | 1.9 | 3.9 | 3.3 | 3 | 3.2 | 4.5 |

TABLE 9

| N5 Pedis Area $mm^2$ | 0 hr | 3 hr | 6 hr | 12 hr | 24 hr | 36 hr | 48 hr |
|---|---|---|---|---|---|---|---|
| 1 | 100 | 137.1 | 138.1 | 125.7 | 125.7 | 120 | 120 |
| 2 | 100 | 139.2 | 144.3 | 124.7 | 161.6 | 118.6 | 117.5 |
| 3 | 100 | 143.9 | 146.9 | 140.8 | 128.6 | 127.6 | 130.6 |
| 4 | 100 | 132 | 145.4 | 141.2 | 142.3 | 142.3 | 142.3 |
| Mean | 100 | 138.1 | 143.7 | 133.1 | 129.6 | 127.1 | 127.6 |
| SD | 0 | 4.9 | 3.9 | 9.1 | 9 | 10.9 | 11.3 |
| SE | 0 | 2.5 | 2 | 4.6 | 4.5 | 5.5 | 5.7 |

TABLE 10

| Hydrocortisone Cream Pedis Area mm² | 0 hr | 3 hr | 6 hr | 12 hr | 24 hr | 36 hr | 48 hr |
|---|---|---|---|---|---|---|---|
| 1 | 100 | 138.1 | 138.1 | 124.8 | 117.1 | 117.1 | 120 |
| 2 | 100 | 133 | 137 | 129 | 128 | 128 | 127 |
| 3 | 100 | 122.7 | 131.8 | 121.8 | 107.3 | 102.7 | 102.7 |
| 4 | 100 | 125.2 | 129.1 | 123.3 | 118.4 | 117.5 | 121.4 |
| Mean | 100 | 129.8 | 134 | 124.7 | 117.7 | 116.3 | 117.8 |
| SD | 0 | 7.1 | 4.3 | 3.1 | 8.5 | 10.4 | 10.5 |
| SE | 0 | 3.6 | 2.2 | 1.6 | 4.3 | 5.2 | 5.3 |

TABLE 11

| Lidex Cream Pedis Area mm² | 0 hr | 3 hr | 6 hr | 12 hr | 24 hr | 36 hr | 48 hr |
|---|---|---|---|---|---|---|---|
| 1 | 100 | 138.8 | 152.4 | 133 | 123.3 | 111.7 | 107.8 |
| 2 | 100 | 139.2 | 130.4 | 119.6 | 112.7 | 109.8 | 107.8 |
| 3 | 100 | 134.3 | 135.2 | 134.3 | 113.3 | 105.7 | 105.7 |
| 4 | 100 | 134.4 | 130.6 | 119.8 | 111.7 | 106.3 | 105.4 |
| Mean | 100 | 136.2 | 137.2 | 126.7 | 115.3 | 108.4 | 106.7 |
| SD | 0 | 3.4 | 10.4 | 8.1 | 5.4 | 2.9 | 1.3 |
| SE | 0 | 1.7 | 5.2 | 4.1 | 2.7 | 1.5 | 0.7 |

Figure 3:
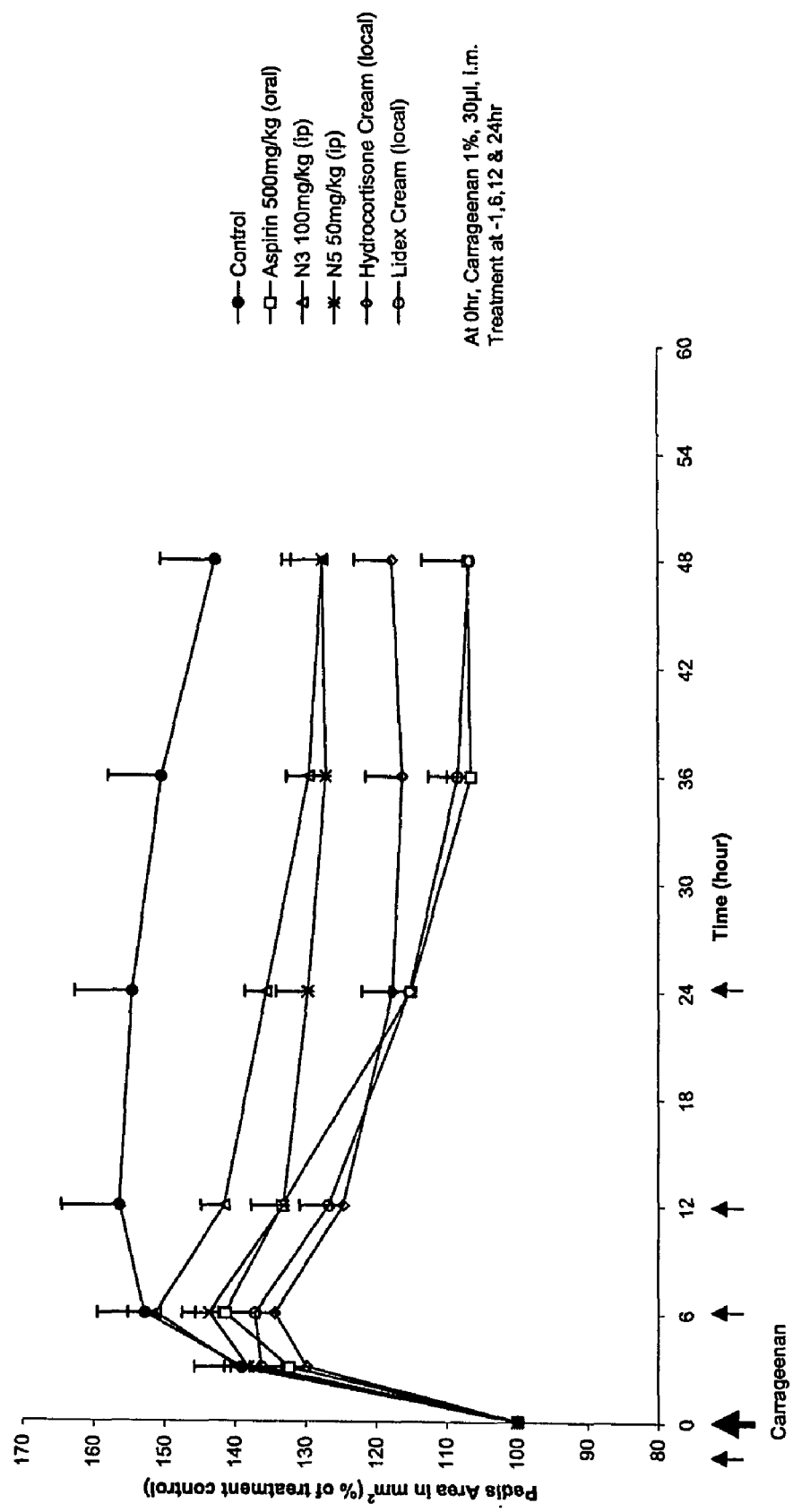
FIG. 3 depicts the anti-inflammatory effects of N3, N5, aspirin, hydrocortisone and lidex against carrageenan-induced paw edema in B6D2F1 mice.

As shown in FIG. 3, all drugs tested showed significant anti-inflammatory effect at 12-48 hours, with the maximal anti-inflammatory effect observed at 24 and 48 hours. The observed potency of anti-inflammatory effect (despite of different doses and modes of administration), were in the following order: Lidex (0.05%, local)≧Aspirin at 500 mg/kg (oral)>Hydrocortisone cream (1%, local)>N5 (50 mg/kg, i.p.)≧N3 (100 mg/kg, i.p.). As shown in FIG. 3, N3 and N5 produced an anti-inflammatory effect when given by intraperitonial injections.

I claim:

1. A method for providing immunosuppression to a mammalian subject in whom an organ has been, comprising administering to the subject one or more ningalins selected from the group consisting of N3, N5 and N6 in an amount effective to decrease inflammatory cell activation at the time of, or following transplantation.

2. The method of claim 1, wherein the subject is a human.

3. The method of claim 1, wherein the subject is having, the adverse immune response.

4. The method of claim 1, wherein the amount administered to the subject is from about 50 to about 500 $mg/m^2$ of one or more ningalins per dose.

5. The method of claim 1, wherein the amount administered to the subject is from about 500 to about 1000 $mg/m^2$ of one or more ningalins per dose.

6. The method of claim 1, wherein the amount administered to the subject is from about 1000 to about 2000 $mg/m^2$ of one or more ningalins per dose.

7. The method of claim 1, wherein the amount administered to the subject is from about 2000 to about 4000 $mg/m^2$ of one or more ningalins per dose.

8. The method of claim 1, wherein the organ is selected from the group consisting of skin, appendix, intestine, stomach, esophagus, duodenum, colon, lung, pharynx, larynx, eye, gum, liver, kidney, bladder, heart, breast, muscle, ear, pancreas, bone and bone marrow.

9. The method of claim 1, wherein the inflammatory cells are selected from the group consisting of leukocytes, lymphocytes, natural killer cells, and antigen-presenting cells.

10. The method of claim 9, wherein the leukocytes are selected from the group consisting of neutrophils, basophils, mast cells, eosinophils, monocytes, and macrophages.

11. The method of claim 9, wherein the lymphocytes are B-lymphocytes or T-lymphocytes.

12. The method of claim 9, wherein the antigen-presenting cells are dendritic cells or stromal cells.

* * * * *

UNITED STATES PATENT AND TRADEMARK OFFICE
CERTIFICATE OF CORRECTION

| | | |
|---|---|---|
| PATENT NO. | : 8,138,170 B2 | |
| APPLICATION NO. | : 11/661522 | |
| DATED | : March 20, 2012 | |
| INVENTOR(S) | : Ting-Chao Chou | |

It is certified that error appears in the above-identified patent and that said Letters Patent is hereby corrected as shown below:

At column 30, claim number 1, line number 3, "has been," should read -- has been transplanted, --

At column 30, claim number 3, line number 9, "subject is having, the" should read -- subject is having an --

Signed and Sealed this
Twelfth Day of June, 2012

David J. Kappos
*Director of the United States Patent and Trademark Office*